US00PP26090P2

(12) United States Plant Patent
Lannes

(10) Patent No.: US PP26,090 P2
(45) Date of Patent: Nov. 17, 2015

(54) ***HIBISCUS* PLANT NAMED 'LANLOIRE'**

(50) Latin Name: *Hibiscus rosa-sinensis*
Varietal Denomination: Lanloire

(71) Applicant: Robert Lannes, Malause (FR)

(72) Inventor: Robert Lannes, Malause (FR)

( * ) Notice: Subject to any disclaimer, the term of this patent is extended or adjusted under 35 U.S.C. 154(b) by 186 days.

(21) Appl. No.: 13/987,552

(22) Filed: Aug. 6, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

(56) References Cited

PUBLICATIONS

CPVO Community Plant Variety Office, Official Gazette of the Community Plant Variety Office Apr. 2011, pp. 32 and 49.*

* cited by examiner

*Primary Examiner* — June Hwu
(74) *Attorney, Agent, or Firm* — Penny J. Aguirre

(57) ABSTRACT

A new cultivar of *Hibiscus* named 'Lanloire', characterized by its large flowers that are rose pink in color with a white eye, its short leaf internode lengths, its very dark green foliage, its good self-branching, and its very vigorous growth habit.

2 Drawing Sheets

Botanical classification: *Hibiscus rosa-sinensis*.
Cultivar designation: 'Lanloire'.

BACKGROUND OF THE INVENTION

The present invention relates to a new and distinct cultivar of *Hibiscus* plant of hybrid origin, botanically known as *Hibiscus rosa-sinensis* 'Lanloire' and will be referred to hereafter by its cultivar name, 'Lanloire'. 'Lanloire' is a new cultivar of tropical *Hibiscus* grown for use as a landscape and container plant.

The new cultivar was developed through an on-going breeding program conducted by the Inventor in Malause, France. The objectives of the breeding program are to develop new cultivars of *Hibiscus* that exhibit compact plant habits with self-branching and a well-balanced plant habit.

The Inventor made a cross in July of 2005 between unnamed proprietary plants in his breeding line; the female parent designated as #F12 and the male parent designated as #M49. 'Lanloire' was selected as a single unique plant from the resulting seedlings in September of 2009.

Asexual propagation of the new cultivar was first accomplished by stem cuttings in Malause, France in September of 2009 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics 'Lanloire'. These attributes in combination distinguish 'Lanloire' as a new and distinct cultivar of *Hibiscus*.

1. 'Lanloire' exhibits large flowers that are rose pink in color with a white eye.

2. 'Lanloire' exhibits short leaf internode lengths.
3. 'Lanloire' exhibits very dark green foliage.
4. 'Lanloire' exhibits good self-branching.
5. 'Lanloire' exhibits a very vigorous growth habit.

The female parent of 'Lanloire', designated as #F12, differs from 'Lanloire' in having smaller flowers that are darker pink in color and in having poor branching. The male parent of 'Lanloire', designated as #M49, differs from 'Lanloire' in having smaller flowers that lack a white eye and in having poor branching. 'Lanloire' can also be most closely compared to the cultivars 'Maia' (not patented) and 'Venetie' (syn. 'Hiven', not patented). Both are similar to 'Lanloire' in flower color. 'Maia' differs from 'Lanloire' in having flowers that are much smaller, double, and in lacking a white eye, and in having less vigor and longer leaf internodes. 'Venetie' differs from 'Lanloire' in having flowers that are smaller, lighter in color, and have a red eye, and in blooming later in the season.

BRIEF DESCRIPTION OF THE DRAWING

The accompanying colored photograph illustrates the overall appearance and distinct characteristics of the new *Hibiscus*. The photographs were taken of a six month-old plant of 'Lanloire' as grown in a one-gallon container in a greenhouse in Malause, France.

The photograph in FIG. 1 provides a side view of 'Lanloire' in bloom.

Figure 1:
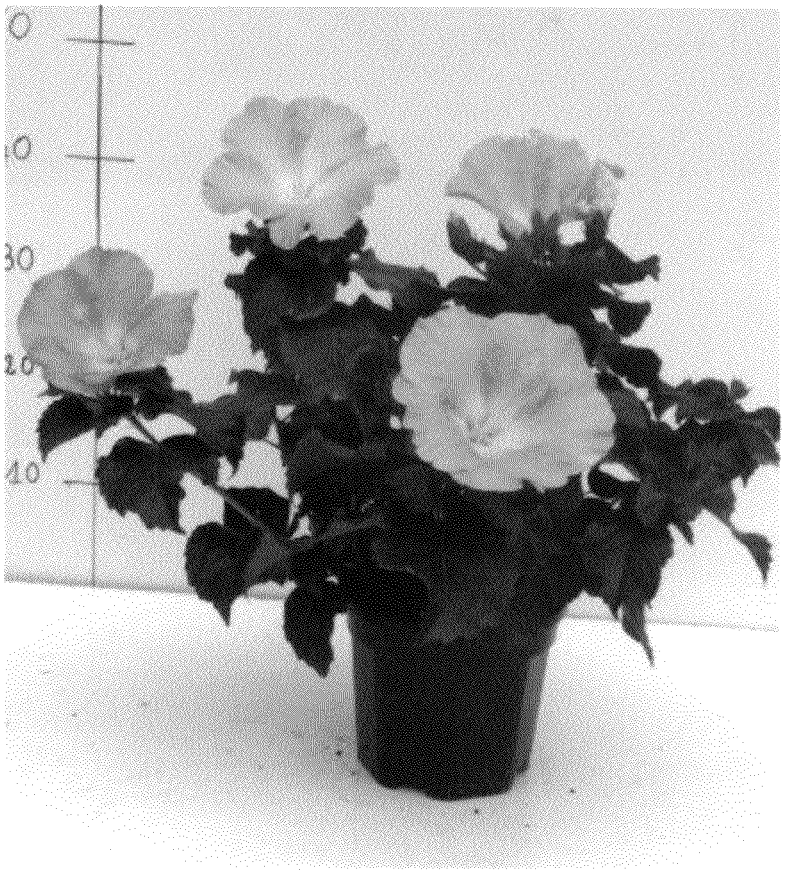
Figure 2:
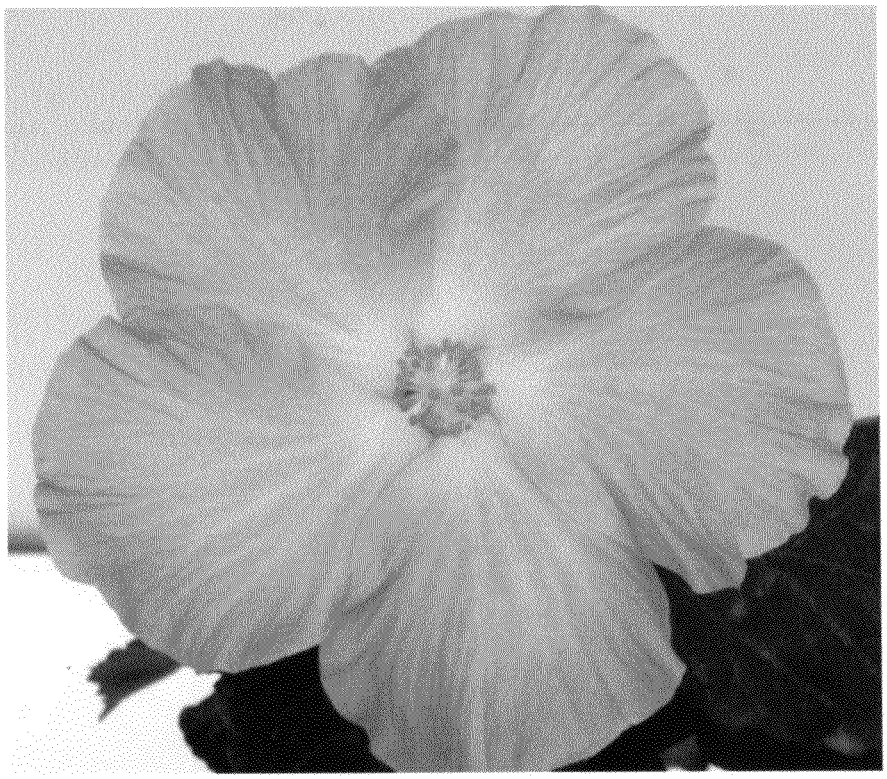

The photograph in FIG. 2 provides a close-up view of a flower of 'Lanloire'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 6 month-old plants of the new cultivar as grown in one-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Continuously through summer in Grand Saline, Tex. and Malause, France.

*Plant type*.—Tropical evergreen shrub.

*Plant habit*.—Upright and slightly spreading, compact.

*Height and spread*.—Reaches 35 to 45 cm in height and 40 to 50 cm in spread.

*Hardiness*.—At least in U.S.D.A. Zones 9 to 11.

*Diseases*.—Not susceptible or resistance to diseases has been observed.

*Root description*.—Fibrous roots.

*Propagation*.—Stem cutting.

*Growth rate*.—Very vigorous.

Stem description:

*Shape*.—Slightly oval.

*Stem color*.—New growth; a blend of 144A and 144B, mature wood; 156A with striations of 138C.

*Stem size*.—Main stems; an average of 5 cm in length and 8 mm in width, lateral stems; an average of 20 cm in length and 4 mm in diameter.

*Stem surface*.—New growth; sparsely pubescent and satiny, bark; finely striated.

*Stem aspect*.—Held at an average angle of 20° (0°=vertical).

*Stem strength*.—Strong.

*Branching*.—Self-branching, an average of 2 main stems and 5 lateral branches per main stem in a one gallon container.

*Internode*.—Average of 4 cm.

Foliage description:

*Leaf shape*.—Ovate.

*Leaf division*.—Simple.

*Leaf base*.—Rounded.

*Leaf apex*.—Acute.

*Leaf venation*.—Pinnate, upper surface 138B in color, lower surface 145C in color.

*Leaf margins*.—Coarsely serrate.

*Leaf attachment*.—Petiolate.

*Leaf arrangement*.—Alternate.

*Leaf orientation*.—Held horizontal.

*Leaf aspect*.—Slightly cupped inward.

*Leaf surface*.—Upper surface glabrous and glossy, lower surface finely pubescent and satiny.

*Leaf color*.—Young leaves upper and lower surface; 144A, mature leaves upper surface; 139A, mature leaves lower surface; 146A.

*Leaf size*.—Average of 8 cm in length, and 6 cm in width.

*Leaf quantity*.—About 7 leaves per lateral branch 20 cm in length.

*Petioles*.—Average of 1.5 cm in length and 1.5 mm in diameter, 144A in color, finely pubescent surface.

Flower description:

*Inflorescence type*.—Flowers are solitary.

*Lastingness of flowers*.—About 1 day, self cleaning.

*Flower size*.—An average of 9 cm in depth (including reproductive organs, without 4 cm) and 11.5 cm in diameter.

*Flower fragrance*.—None.

*Flower shape*.—Rotate.

*Flower number*.—Average of 3 per lateral stem at one time, continuously produces throughout the summer.

*Flower aspect*.—Outward to slightly reflexed.

*Flower bud*.—Elliptic in shape, an average of 5.5 cm in length and 1.8 cm in width, color sepal portion; a blend of 144A and 144B, apex (petal portion); a blend of 150D and suffused with 39B.

*Flower attachment*.—Peduncle.

*Petal number*.—5.

*Petal shape*.—Obcordate.

*Petal color*.—Upper surface when opening and fully opened; a blend of 62B and 62C, and blending into NN155B at base of petal and having a small spot of 63B on margins at base, lower surface when opening and fully opened; a blend of 63C and 63D and blending into NN155B at base of petal and having a small spot of 63B on margins at base.

*Petal surface*.—Both surfaces smooth and dull on upper portion and satiny near base.

*Petal margins*.—Very slightly crenated and slightly wavy.

*Petal apex*.—Rounded.

*Petal base*.—Slightly oblique and adnate to base of style.

*Petal size*.—Average of 7 cm in length and 6 cm in width.

*Sepal number*.—5.

*Sepal shape*.—Elliptic.

*Sepal margin*.—Entire.

*Sepal size*.—Average of 2.5 cm in length and 9 mm in width.

*Sepal aspect*.—Upright, lower 50% fused.

*Sepal surface*.—Upper (outer) surface pubescent, lower surface (inner) smooth and glossy.

*Sepal apex*.—Acute-slightly acuminate.

*Sepal base*.—Fused.

*Sepal color*.—Young and mature upper (outer) and lower (inner) surface; a blend of 144A and 144B.

*Calyx*.—Campanulate in shape, average of 2.5 cm in length and 1.8 cm in diameter.

*Peduncles*.—An average of 3 cm in length (including a 3 mm segment towards base of flower that is wider and separated by a ligule) and 2 mm in diameter, strong, average angle is 45° and 144B in color with ligule 144A, finely pubescent surface.

*Pedicels*.—Not present, flowers are solitary from terminal leaf axils.

*Bracts*.—Average of 7 bracts held upright surrounding sepals, lanceolate-linear in shape, narrowly acute apex, truncate base, average of 1 cm in length and 1.5 mm in width, a color between 144A and 137D in color on inner and outer surface, surface is slightly pubescent on inner and outer surface.

Reproductive organs:

*Gynoecium*.—1 pistil, about 9 cm in length, stigmas; club-shaped, an average of 5, and 17C in color, style;

6.5 cm in length and 158C in color, ovary; 7 mm in length and 6 mm in width, 150C in color and is completely covered by the base of the pistil style.

*Androecium*.—Stamens; average of 60, stamens are clustered and implanted into upper portion of style, anthers; dorsifixed and orbicular in shape, 1 mm in diameter, and 160D in color; filament; 4.5 mm in length, 0.3 mm in width, and 155A in color, pollen; abundant in quantity and 17A in color.

*Fruit/seeds*.—None observed.

It is claimed:

1. A new and distinct cultivar of *Hibiscus* plant named 'Lanloire' as herein illustrated and described.

* * * * *